United States Patent [19]  [11] 4,024,156
Bagli et al. [45] May 17, 1977

[54] THIOPHENE ETHANOLAMINES

[75] Inventors: Jehan F. Bagli, Kirkland; Eckhardt Ferdinandi, St. Laurent, both of Canada

[73] Assignee: American Home Products Corporation, New York, N.Y.

[22] Filed: Apr. 18, 1975

[21] Appl. No.: 569,509

[30] Foreign Application Priority Data

Apr. 18, 1974 Canada .............................. 197896

[52] U.S. Cl. .................. 260/332.3 R; 260/268 PH; 260/319.1; 260/332.3 P
[51] Int. Cl.$^2$ ............. C07D 333/08; C07D 333/10
[58] Field of Search ............................ 260/332.3 R

[56] References Cited
UNITED STATES PATENTS 3,687,945  8/1972  Thiele et al. ................ 260/332.3 R
3,766,173  10/1973  Thiele et al. ................ 260/332.3 R

OTHER PUBLICATIONS

V. P. Arya et al., *J. of Pharmaceutical Sciences*, vol. 58, pp. 432–440, (1969).
Prabhash Chandra Das et al., *J. of Medicinal Chemistry*, vol. 14, No. 9, pp. 890–891.
Kurt Thiele et al., *Chemical Abstracts*, vol. 71, 91188x, (1969).

*Primary Examiner*—Donald G. Daus
*Assistant Examiner*—Jose Tovar
*Attorney, Agent, or Firm*—Stephen Venetianer

[57] ABSTRACT

Thiophene ethanolamines substituted on the nitrogen atom with an alkyl or aralkyl radical and optionally substituted on the thiophene portion, are disclosed. The thiophene ethanolamines possess antihypertensive and β-receptor blocking activities. Methods for their preparation and use are given.

26 Claims, No Drawings

THIOPHENE ETHANOLAMINES

BACKGROUND OF THE INVENTION a. Field of the Invention

This invention relates to thiophene ethanolamines, to processes for their preparation and to intermediates therefor.

More specifically, the compounds of this invention are thiophene ethanolamines characterized further in that they are substituted on the nitrogen atom with an alkyl or an aralkyl radial and are optionally substituted on the thiophene portion.

b. Description of the Prior Art

The prior art relating to thiophene ethanolamines is rather niggardly. An early report by C. F. Heubner, et al., J. Org. Chem., 18, 21 (1953), described the preparation of the thiophene ethanolamine, α-(aminomethyl)thiophene-2-methanol, which was found to have pressor activity. In 1968, E. D. Bergmann and Z. Goldschmidt, J. Med. Chem., 11, 1121 (1968), described soem corresponding N-alkyl derivatives of the latter thiophene ethanolamine, noting that these derivatives possessed no significant pharmacologic activity. A still more recent report, C. Carrol, et al., J. Med. Chem., 16, 882 (1973), described a related series of N-substituted thiophene ethanolamines, the substitution being alkyl, phenyl or such that the nitrogen atom forms part of a pyrrolidine, piperidine or morpholine ring. A variety of pharmacologic properties properties were reported for the series including the property that they antagonized the hypotensive response to isoproterenol.

Unexpectedly, we have found that the compounds of the present invention, and particularly the N-(aralkyl)-thiophene ethanolamines are potent antihypertensive and β-receptor blocking agents. These properties together with their relatively low toxicity and the direct manner in which these compounds are prepared render them useful and practical for the treatment of hypertensive conditions and lessening undersirable β-adrenergic stimulation of the myocardium.

SUMMARY OF THE INVENTION

The thiophene ethanolamines of this invention are represented generally by the formula Ar-CHOR$^1$CHR$^2$NR$^3$R$^4$ in which Ar is the radical

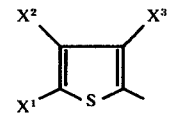

wherein X$^1$, X$^2$ and X$^3$ are selected from the group consisting of hydrogen, halo, lower alkyl, lower alkoxy and phenyl; R$^1$ is hydrogen or lower alkyl, R$^2$ is hydrogen or lower alkyl; R$^3$ is hydrogen or lower alkyl; and R$^4$ is lower alkyl, 2-indol-3-ylethyl or a phenethyl radical of the formula,

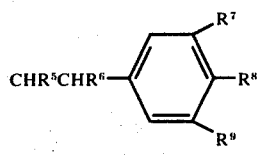

wherein R$^5$ is hydrogen or lower alkyl, R$^6$ is hydrogen or hydroxy and R$^7$, R$^8$ and R$^9$ are the same or different selected from the group consisting of hydrogen, lower alkyl, lower alkoxy, hydroxy and halo, or R$^6$ and R$^7$ are joined to form a methylenedioxy radical and R$^8$ is hydrogen; or R$^3$ and R$^4$ together with the nitrogen to which they are joined form a 4-phenyl-, 4-(4-methoxyphenyl)- or 4-(o-tolyl)-piperazin-l-yl group with the proviso that when Ar is the radical

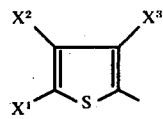

wherein X$^1$, X$^2$ and X$^3$ are selected from the group consisting of hydrogen or halo, R$^4$ is other than lower alkyl as defined herein; and by the formula ArCH(CHR$^2$OH)NR$^3$R$^4$ in which Ar, R$^2$, R$^3$ and R$^4$ are as defined herein.

The preferred ethanolamines of this invention are represented by the formula

ArCHOR$^1$CHR$^2$NR$^3$R$^4$ in which Ar is selected from the group consisting of 2-thienyl, 5-(lower alkyl)-2-thienyl, 5-phenyl-2-thienyl and 4,5-dichloro-2-thienyl; R$^1$ is hydrogen or lower alkyl; R$^2$ is hydrogen or lower alkyl; R$^3$ is hydrogen or lower alkyl; and R$^4$ is 2-indol-3-ylethyl, a substituted phenethyl of the formula

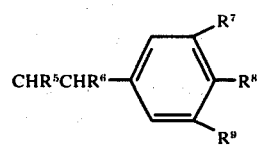

wherein R$^5$ is hydrogen or lower alkyl, R$^6$ is hydrogen or hydroxy and R$^7$, R$^8$ and R$^9$ are the same or different selected from the group consisting of hydrogen, lower alkyl, lower alkoxy, hydroxy and halo or R$^7$ and R$^8$ are joined to form a methylenedioxy radical and R$^9$ is hydrogen; or R$^3$ and R$^4$ together with the nitrogen to which they are joined form a 4-(4-methoxyphenyl)- or 4-(o-tolyl)-piperazin-l-yl group; and by the formula ArCH(CHR$^2$OH)NR$^3$R$^4$ in which Ar, R$^{2,}$ R$^3$, and R$^4$ are as defined herein.

DETAILED DESCRIPTION OF THE INVENTION

The term lower alkyl as used herein contemplates straight chain alkyl radicals containing from one to six carbon atoms and branched chain alkyl radicals containing from three to four carbon atoms and includes methyl, ethyl, propyl, isopropyl, butyl, isobutyl, 2-methylpentyl, hexyl and the like.

The term lower alkoxy as used herein contemplates both straight and branched chain alkoxy radicals containing from one to four carbon atoms and includes methoxy, ethoxy, isopropoxy, t-butoxy and the like.

The term halo as used herein contemplates halogens and includes chlorine, bromine and iodine.

The term alkanoyl as used herein contemplates the radical COCH$_2$R$^2$ in which R$^2$ is hydrogen or lower alkyl as defined herein.

The compounds of this invention form salts with pharmaceutically acceptable acids. Such acid additions salts are included within the scope of this invention.

The acid addition salts are prepared by reacting the corresponding base form of the thiophene ethanolamine with at least one equivalent, or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, oxalate, maleate, citrate, hydrobromide and hydrochloride. Both the base compounds and the salts have the distinct advantage of possessing a relatively low order of toxicity.

The stereochemical isomers of the compounds of this invention, made possible by the occurrence of asymmetric centers contained therein, are also included within the scope of this invention.

The antihypertensive effect of the compounds of this invention and their acid addition salts is demonstrated in standard tests, for example, in tests conducted in the spontaneously hypertensive rat such as described by I. Vavra, et al., Can. J. Physiol. Pharmacol., 51 727 (1973). For instance, the following compounds have been found to be active in this test at 50 mg/kg or less when they are given by gavage as a single dose.

α-{[3,4-dimethoxyphenethyl)amino]methyl}-2-thiophenemethanol oxalate (Example 15),
α-{[3,4-dimethoxyphenethyl)amino]methyl}-5-methyl-2-thiophenemethanol oxalate (Example 16), and
α-{[(3,4-dimethoxyphenethyl)amino]methyl}-5-phenyl-2-thiophenemethanol hydrochloride (Example 19).

Thus an embodiment of this invention includes the method of lowering blood pressure in a hypertensive host such as a mammal by administering a therapeutically effective amount of the compounds of this invention to the host.

The β-receptor blocking activity of the compounds and their acid addition salts is demonstrated also in standard tests such as those described by E. Westermann and K. Stock in "International Symposium on Drugs Affecting Lipid Metabolism, 3rd, Milan, 1968", W. J. Holmes, et al., Ed., Plenum Press, New York, 1969, pp 45 – 61.

When the compounds of this invention and their acid addition salts are employed as antihypertensive or β-receptor blocking agents in warm-blooded mammals, e.g. rats and mice, they are used alone or in combination with pharmacologically acceptable carriers. The proportion of the compound is determined by its solubility and chemical nature, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they are used in the form of a sterile solution containing other solutes, for example, enough saline or glucose to make the solution isotonic.

The dosage of the present therapeutic agents will vary with the form of administration and the particular compound chosen. Futhermore, it will vary with the particular host under treatment. Generally, treatment is initiated with small dosages substantially less than the optimum dose of the compound. Thereafter, the dosage is increased by small increments until the optimum effect under the circumstance is reached. In general, the compounds of this invention are most desirably administered at a concentration level that will generally afford effective results without causing any harmful or deleterious side effects and preferably at a level that is in a range of from about 0.1 mg to about 100 mg per kilo per day, although as aforementioned variations will occur. However, a dosage level that is in the range of from about 5.0 mg to about 50 mg per kilo per day is most desirably employed in order to achieve effective results.

PROCESS

One method for preparing the compounds of this invention is illustrated as follows:

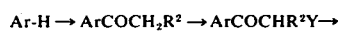

in which $R^1$ is hydrogen, Y is bromo, chloro or iodo and Ar, $R^2$, $R^3$ and $R^4$ are as defined herein.

The requisite starting materials of formula Ar—H are either known or are prepared readily by known methods. Examples of the known thiophene starting materials include the commercially available 2-chlorothiophene and 2-bromothiophene. 2,3-Dibromothiophene is described by S. O. Lawesson, Arkiv. Kemi, 11, 378 (1957), 3,4-dibromothiophene is described by S. Gronowitz, Acta Chem. Scand., 13, 1045 (1959), 2,3-dichlorothiophene, 3,4-dichlorothiophene are described by Corral, et al., cited above, 2-methoxythiophene is described by J. Sice, J. Amer. Chem. Soc., 75, 3697 (1953), 3,4-dimethoxy thiophene is described by E. W. Fager, J. Amer. Chem. Soc., 67, 2217 (1945), 2-methylthiophene is described by F. S. Fawcett, J. Amer. Chem. Soc., 68, 1420 (1946) and 2-phenylthiophene is described by A. I. Kosak, et al., J. Amer. Chem. Soc., 76, 4450 (1954).

General methods for making any of the halo, alkyl, alkoxy, and aryl thiophenes of formula Ar—H are described in general testbooks; for example, Rodd's Chemistry of Carbon Compounds, 2nd ed., S. Coffey, Ed., Vol. IV-A, Elsevier Scientific Publishing Co., Amsterdam, 1973 pp 220 – 255 and "Heterocyclic Compounds", R. C. Elderfield, Ed., Vol. 1, John Wiley & Sons, Inc., New York and London, 1950, pp 208 – 276.

With reference to the process the thiophene starting materials of formula Ar—H are subjected to acylation to give the corresponding 2-acylthiophene derivatives of formula $ArCOCH_2R^2$ in which Ar and $R^2$ are as defined above. Although a variety of methods are reported for accomplishing this acylation, see for example the aforementioned textbooks, a preferred method for obtaining the 2-acylthiophene derivatives of formula $ArCOCH_2R^2$ in which $R^2$ is hydrogen or lower alkyl involves treating the appropriate thiophene of formula Ar—H with an appropriate alkanoyl chloride or bromide, for example, acetyl chloride or propionyl bromide, in an inert organic solvent, preferably benzene or toluene, at temperatures ranging from −20° to 80° C, preferably 0° to 30° C for 2 to 72 hours, preferably 6 to 72 hours.

Alternatively, the 2-acylthiophenes are prepared from the appropriate thiophene of formula Ar—H according to a modification of the method of W. Steinkopf and W. Kohler, Justus Liebigs' Ann. Chem., 532.

250 (1937). The latter method involves treating the thiophene with an organic lithium reagent, preferably n-butyl lithium in an inert solvent, preferably tetrahydrofuran, ether, hexane and the like, to generate the corresponding 2-thienyl lithium derivative. The latter derivative is reacted with carbon dioxide to give the corresponding 2-thiophene carboxylic acid which on treatment with the appropriate lower alkyl lithium gives the desired 2-acylthiophene.

A number of the 2-acylthiophenes utilized in the process of this invention are known; for example, 2-acetylthiophene described by J. R. Johnson and G. E. May, Org. Synth., 18, 1 (1938 ); 2-propionylthiophene, described by H. A. Bruson and T. W. Riener, J. Amer. Chem. Soc. 70, 214 (1948) and 2-acetyl-3,4-dichlorothiophene described by E. Profft and G. Solf, J. Prakt. Chem., 24, 38 (1964). See also the general textbooks noted above.

In the next step the 2-acylthiophene is converted by halogenation to the corresponding haloketone of formula ArCOCHR$^2$Y in which R$^2$ is hydrogen or lower alkyl and Y is bromo, chloro or iodo. This conversion is accomplished readily by halogenating agents known to be effective for introducing a halogen atom α to a ketone. In a preferred embodiment of this conversion the halogenation is effected with substantially an equimolar amount of elemental bromine, pyridumium bromide or cupric bromide in an inert organic solvent, preferably chloroform or acetic acid, to obtain the corresponding bromoketone, ArCOCHR$^2$Br. Similar conversions to the corresponding chloroketone or iodoketone are accomplished with elemental chlorine or iodine, respectively. In these cases the halogenation proceeds readily. Convenient times and temperatures include 10 to 60 minutes and 0° to 30° C.

Several of the haloketones of formula ArCOCHR$^2$Y have been described previously; for example 2-(bromoacetyl)thiophene, described by Heubner, et al., cited above, 2-(chloroacetyl)thiophene, described by W. S. Emerson and T. M. Patrick, J. Org. Chem., 13, 724 (1948) and 2-(chloroacetyl)-3,4-dichlorothiophene, described by Profft and Solf, cited above.

In the next step the α-haloketone of formula ArCHOCHR$^2$Y in which Ar, R$^2$ and Y are as defined herein is reduced with a complex metal hydride to give the corresponding halohydrin of formula ArCHOCHR$^2$Y. Examples of suitable complex metal hydrides for this reduction are sodium borohydride, lithium aluminium hydride and diborane. Sodium borohydride is preferred. The reduction is carried out in a non-reactive solvent medium. When sodium borohydride is used, preferred solvents include methanol or tetrahydrofuran. When lithium aluminum and diborane are used as the reducing agent, preferred solvents include the non-hydroxylic solvents, for example, diethyl ether, dioxane, tetrahydrofuran, 1,2-dimethoxyethane and the like. Generally the reaction is best performed at temperatures ranging from 0° to 40° C for periods varying from 30 minutes to 24 hours. While equivalent quantities of reactants may be used, it is preferable to use the reducing agent in moderate excess.

The halohydrin so obtained is used thereafter for N-alkylaytion of the appropriate primary or secondary amine of formhula NHR$^3$R$^4$ to obtain the corresponding thiophene ethanolamine of formula ArCHOR$^1$CHR$^2$NR$^3$R$^4$ in which R$^1$ is hydrogen and R$^2$, R$^3$ and R$^4$ are as defined herein. One method for effecting this N-alkylation includes bringing the reactants together in the presence of a base; suitable bases for this purpose are alkali metal carbonates and alkali metal bicarbonates. The ratio of reactants will depend on the starting material that is employed and the product that is desired. When the starting material is a primary amine, a secondary amine product is obtained by using slightly more than one equivalent of alkylating agent and base, whereas a tertiary amine product is obtained by using somewhat more than two equivalents of alkylating agent and base. When the starting material is a secondary amine, a tertiary amine product is obtained by using slightly more than one equivalent of alkylating agent and base. Depending upon the particular alkylating agent and base chosen, a variety of solvents and reaction conditions may be used. Some examples of suitable solvents are aromatic hydrocarbons, ethers, lower alkanols, lower aliphatic ketones, and other non-reactive solvents, such as dimethyl sulfoxide, N,N-dimethylformamide, and and acetonitrile. The temperature and duration of the reaction are not critical and may be varied over a wide range, depending upon the particular alkylating agent and solvent that are used. Generally it is most conveninet and efficacious to carry out the reaction at the reflux temperature of the reaction mixture for a period of 1 hour to several days.

The requisite primary and secondary amines of formula NHR$^3$R$^4$ are either known or are prepared by known methods; for example, see "Methoden der Organic Chemie", (Hobuen-Weyl), E. Muller, Ed., Vol. 11/1, Georg Thieme Verlag, Stuttgart, 1957, pp 9 – 1033.

Using similar N-alkylation conditions any of the aforementioned secondary amines (i.e., compounds of formula ArCHOR$^1$CHR$^2$NR$^3$R$^4$ in which R$^3$ is hydrogen) are converted to corresponding tertiary amines. Preferred conditions include treating the secondary amine with about five to ten molar equivalents of the appropriate lower alkyl halide or aralkyl halide in an inert organic solvent, for instance, ethanol, tetrahydrofuran or benzene, from 1 to 24 hours or more at a temperature ranging from about 20° – 80° C.

In a preferred embodiment of the process the N-alkylation is effected by heating the bromohydrin with 1.0 to 1.5 molar equivalents of the primary or secondary amine either together in a pressurized container at 80° – 120° C or at 40° to 120° C in the presence of an inert organic solvent. Generally the reactants are heated together for 3 to 24 hours. Preferred solvents for this latter conditions include benzene, toluene, dioxane and tetrahydrofuran.

It should be noted that in the aforementioned N-alkylation reactions, a by-product is sometimes encountered. This by-product is isomeric to the expected thiophene ethanol and has the general formula ArCH(CHR$^2$OH)NR$^3$R$^4$ in which Ar, R$^2$, R$^3$ and R$^4$ are as defined herein. These isomers also psosess usefule antihypertensive properties as demonstrated in the above tests. Accordingly, these isomers and their corresponding acid addition salts with pharmaceutically acceptable acids can be formulated and used for this purpose in the manner described above for the thiophene ethanolamines.

In the case where the thiophene ethanolamines of this invention are the compounds of formula ArCHOR$^1$CHR$^2$NR$^3$R$^4$ in which R$^1$ and R$^2$ are hydrogen, R$^3$ and R$^4$ are as defined herein and Ar is the radical

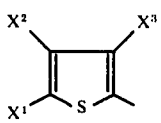

wherein $X^1$, $X^2$ and $X^3$ are selected from the group of hydrogen and lower alkoxy with the proviso that at least one of $X^1$, $X^2$ or $X^3$ is lower alkoxy, the following alternative procedure has been found to be convenient:

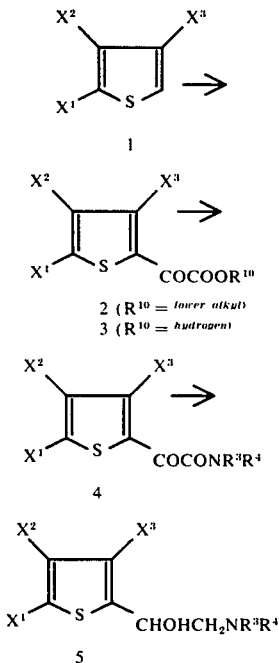

in which $X^1$, $X^2$ and $X^3$ are as defined in the last instance and $R^3$ and $R^4$ is as defined herein.

With reference to this latter process the substituted thiophene of formula 1 is reacted with a organolithium reagent in an inert solvent. Suitable organolithium reagents include n-butyl lithium, n-propyl lithium, phenyl lithium and the like. Suitable inert solvents include ether, tetrahydrofuran, hexane and the like. In this manner the corresponding thienyl lithium derivative is generated. The lithium derivative is then reacted with a dialkyl oxalate, preferably dimethyl oxalate, to give the corresponding ester of formula 2 in which $R^{10}$ is lower alkyl, preferably methyl. This ester is then hydrolyzed with a strong base, for example, sodium or potassium hydroxide, in the presence of sufficient water to effect hydrolysis. The hydrolysis is performed using a suitable solvent, for example, methanol or ethanol. The reaction mixture is maintained at a temperature of from 25° C to the reflux temperature of the mixture until hydrolysis occurs, usually from 10 minutes to 6 hours is sufficient. The reaction mixture is then rendered acidic with an acid, for example, acetic acid, hydrochloric acid, sulfuric acid and the like, and the free acid (compound 3) isolated.

At this point the latter free acid is subjected to amidation. This amidation is accomplished readily by first treating the acid with a lower alkyl chloroformate, preferably ethyl chloroformate, in the presence of triethylamine, to afford the corresponding mixed anhydride. Reaction of the mixed anhydride with the appropriate amine of formula $HNR^3R^4$ gives the corresponding amide of formula 4.

Thereafter, treatment of the latter amide with a suitable complex metal hydride yields the corresponding desired thiophene ethanolamine of formula 5. Examples of suitable complex metal hydrides are lithium aluminum hydride, aluminium hydride-aluminum chloride, diborane and sodium borohydrie-aluminum chloride; lithium aluminum hydride being preferred.

In a special modification of the latter step the amide of formula 4 in which $R^3$ is hydrogen is first treated with triethyloxonium fluoroborate in an inert organic solvent, for example, chloroform or methylene dichloride, to give the intermediate iminoether fluoroborate. Subsequent reduction of the latter intermediate with an alkali metal borohydride, preferably sodium borohydride, give the corresponding desired thiophene ethanolamine of formual 5 in which $R^3$ is hydrogen.

Finally, in the case where it is desired to obtain the thiophene ethanolamines of formula $ArCHOR^1CHR^2NR^3R^4$ in which $R^1$ is lower alkyl (i.e., $R^1$ forms part of a lower alkoxy group), the preferred mode of preparation involves a modification of the above process in which the halohydrin of formula $ArCHOHCHR^2Y$ in which Ar, $R^2$ and Y are as defined herein is treated with the appropriate lower alkanol in the presence of an acid catalyst, for example, p-toluenesulfonic acid, sulfuric acid or boron trifluoride etherate, to give the corresponding lower alkoxy derivative of formula $ArCHOR^1CHR^2Y$ in which Ar, $R^2$ and Y are as defined herein and $R^1$ is lower alkyl. Conversion of the latter compound to the corresponding amine in the same manner described hereinbefore gives the thiophene ethanolamines of this ivnention of formula $ArCHOR^1CHR^2NR^3R^4$ in which Ar, $R^2$, $R^3$ and $R^4$ are as defined herein and $R^1$ is lower alkyl.

The following examples illustrate further this invention.

EXAMPLE 1

Acylation - Method A

By following the procedure described by J. R. Johnson and G. E. May, Org. Synth., 18, 1 (1938), for the preparation of 2-acetylthiophene, the following 2-acylthiophenes are obtained:

2-acetyl-5-bromothiophene, mp 94°– 94° C, from 2-bromothiophene and acetyl chloride;

2-acetyl-5-chlorothiophene, mp 46° C, from 2-chlorothiophene and acetyl chloride;

2-acetyl-3,4-dibromothiphene, mp 80°–81° C, from 3,4-dibromithiophene and acetyl chloride; 2-acetyl-4,5-dibromothiophene, mp 84°–85° C, from 2,3-dibromothiophene and acetyl chloride;

2-acetyl-3,4-dichlorothiophene, mp 51°–52° C, from 3,4-dichlorothiophene and acetyl chloride; 2-acetyl-4,5-dichlorothiophene, mp 66°–67° C, from 2,3-dichlorothiophene and acetyl chloride;

2-acetyl-3,4-dimethoxythiophene, mp 102° C, from 3,4-dimethoxybenzene and acetyl chloride;

5-chloro-2-propionylthiophene, mp 50°–51° C, from 2-chlorothiophene and propionyl chloride;

2-acetyl-5-methylthiophene, nmr ($CDCl_3$) δ 2.50 (s, 3H), 2.55 (s, 3H), 6.83 (m, 1H), 7.57 (d, 1H), from 2-methylthiophene and acetyl chloride; and 2-acetyl-5-phenylthiophene, mp 115° C, from 2-phenylthiophene and acetyl chloride.

EXAMPLE 2

Acylation - Method B

Another method for preparing 2-acylthiophenes is exemplified by the following preparation of 2-acetyl-5-phenyl-thiophene:

A solution of 2- phenylthiophene (16.0 g, 0.1 mole) in 100 ml anhydrous tetrahydrofuran (THF) is treated dropwise with a solution of n-butyl lithium (0.11 mole) in hexane (2M solution). Thereafter the mixture is stirred for 1 hr. The resulting black solution is poured onto 50 g of solid $CO_2$ covered with ether. When all the $CO_2$ is evaporated, the mixture is treated with 200 ml of water, acidified with 10% HCl and extracted with ether. The extract is washed with 5% NaOH. The latter washings are cooled and rendered acidic with 20% HCl. The resulting precipitate is collected and recrystallized from 1000 ml $CCl_4$ to give 5-phenyl 2-thiophenecarboxylic acid, mp 180° C, $\gamma_{max}^{CHCl_3}1665$ cm$^{-1}$, as yellow green crystals.

The latter compound (16.7 g, 0.08 mole) in 300 ml of anhydrous ether is cooled to −50° C and treated dropwise with methyl lithium (0.16 mole) in ether (1M solution). The mixture is allowed to warm to 0° C over a period of 2 hr. Thereafter the mixture is poured onto cold 5% HCl and extracted with ether. The extract is washed with 5% $NaHCO_3$, water and brine, dried ($MgSO_4$) and concentrated to give a yellow solid which is purified by chromatography on silica gel to give pure 2-acetyl-5-phenylthiophene, mp 115° C, $\gamma_{max}^{CHCl_3}1650$ cm, identical to the product of the same name described in Example 1.

Other 2-acylthiophenes are obtained by this procedure by utilizing the appropriate thiophene of formula Ar—H; for example, the use of 2,3-dichlorothiophene gives 2-acetyl-4,5-dichlorothiophene.

EXAMPLE 3

HALOGENATION

The haloketones are obtained by procedures which are exemplified as follows:

Method A

A solution of 2-acetyl-5-phenylthiophene (11.7 g, 0.058 mole), described in Examples 1 and 2, in 100 ml of glacial acetic acid is treated dropwise with bromine (9.3 g, 0.058 mole). The mixture is stirred for ½ hr, poured into cold water and extracted with chloroform. The extract is washed with water, 5% $NaHCO_3$ and brine, dried ($H_2CO_3$) and concentrated to give a yellow solid. The solid is subjected to chromatography on silica gel to give bromomethyl 5-phenyl-2-thienyl ketone ($ArCOCHR^2Y$; Ar is 5-phenyl-2-thienyl, $R^2 = H$ and $Y = Br$) mp 114° C.

Method B

A solution of 5-methyl-2-thienyl methyl ketone (24.8 g, 0.177 mole), described in Example 1, in 170 ml chloroform is treated with pyridinium bromide perbromide (56.7 g, 0.177 mole). The mixture is stirred for 2½ hr. The resulting deep red solution is poured into ice water. The mixture is extracted with ether. The extract is washed with water and brine, dried ($MgSO_4$), and concentrated to give a brown liquid. The oil is purified by chromatography on silica gel to give bromomethyl-5-methyl-2-thienyl ketone ($ArCOCHR^2Y$; Ar is 5-methyl-2-thienyl, $R^2 = H$ and $Y = Br$); $\epsilon_{max}^{film}$ 1650 cm$^{-1}$, nmr ($CDCl_3$) $\delta 2.58$ (s, 3H), 4.3 (s, 2H), 6.86 (m, 1H), 7.67 (m, 2H).

Method C (method of L. C. King and G. K. Ostrum, J. Org. Chem., 29, 3459 (1964):

A stirred suspension of cupric bromide (20.7 g) in 50 ml ethyl acetate is heated to reflux. 2-Acetylthiophene (7.0 g) dissolved in 50 ml chloroform is added rapidly from a dropping funnel. The reaction mixture is heated with vigorous stirring until the black cupric bromide had all been converted to the white cuprous bromide (about 2 hr.). The reaction mixture is cooled, filtered and concentrated. The resulting oil is subjected to chromatography on silica gel. Evaporation of the eluant (benzene-hexane, 8:2) gives bromomethyl 2-thienyl ketone ($ArCOCHR^2Y$; Ar is 2-thienyl, $R^2 = H$ and $Y = Br$); bp 100° C/0.2mm, $\gamma_{max}^{CHCl_3}1660$, 1410 cm$^{-1}$.

The following table lists other haloketones prepared by either method A, B or C, as indicated, together with the requisite starting materials described in Example 1.

| STARTING MATERIAL | METHOD | HALOKETONE |
|---|---|---|
| 2-acetyl-5-bromothiophene | A | bromomethyl 5-bromo-2-thienyl ketone, mp 90 – 91° C |
| 2-acetyl-5-chlorothiophene | B | bromomethyl 5-chloro-2-thienyl ketone, mp 72 – 73° C |
| 2-acetyl-3,4-dibromothiophene | C | bromomethyl 3,4-dibromo-2-thienyl ketone, mp 80 – 82° C |
| 2-acetyl-4,5-dibromothiophene | A | bromomethyl 4,5-dibromo-2-thienyl ketone, mp 67.5–70° C |
| 2-acetyl-3,4-dichlorothiophene | C | bromomethyl 3,4-dichloro-2-thienyl ketone, mp 46–47° C |
| 2-acetyl-4,5-dichlorothiophene | B | bromomethyl 4,5-dichloro-2-thienyl ketone, $\gamma_{max}^{CHCl_3}1665, 1520, 1405$ cm$^{-1}$ |
| 2-acetyl-3,4-dimethoxythiophene | B and C | bromomethyl 3,4-dimethoxy-2-thienyl ketone, $\gamma_{max}^{CHCl_3}3120, 1650$ cm$^{-1}$; bromomethyl 5-bromo-3,4-dimethoxy-2-thienyl ketone, mp 94° C, isolated as a by-product (separated by chromatography) when method C is used. |
| 5-chloro-2-propionylthiophene | B | 1-bromomethyl 5-chloro-2-thienyl ketone, $\gamma_{max}^{CHCl_3}1660, 1410$ cm$^{-1}$ |

EXAMPLE 4

Reduction

A solution of the haloketone, bromomethyl 2-thienyl ketone (6.0 g), described in Example 3, in 40 ml of methanol is cooled to 0° C. Sodium borohydride (1.11 g) in 10 ml of methanol is added rapidly to the solution. After 15 minutes the reaction mixture is diluted with ice-water and extracted with ether. The extract is washed with water and brine, dried ($MgSO_4$) and concentrated to give α-(bromomethyl)-2-thiophenemethanol; $\gamma_{max}^{CHCl_3}3550, 3400, 1060, 1035$ cm$^{-1}$ (Ar-CHOHCHR$^2$Y; Ar = 2-thienyl, $R^2 = H$ and $Y = Br$).

By following the procedure of Example 4 and using the appropriate haloketone as starting material the other corresponding halohydrins of formula Ar-CHOHCHR$^2$Y are obtained. Examples of such halohydrins are listed in the following table together with the requisite starting material described in Example 3.

| EXAMPLE | STARTING MATERIAL | HALOHYDRIN |
|---|---|---|
| 5 | bromomethyl 5-bromo-2-thienyl ketone | α-(bromomethyl)-5-bromo-2-thiophenemethanol, $\gamma_{max}^{CHCl_3}$3540, 3400 cm |
| 6 | bromomethyl 5-chloro-2-thienyl ketone | α-(bromomethyl)-5-chloro-2-thiophenemethanol, $\gamma_{max}^{CHCl_3}$3570, 3350, 1062, 1000 cm$^{-1}$ |
| 7 | bromomethyl 3,4-dibromo-2-thienyl ketone | α-(bromomethyl)-3,4-dibromo-2-thiophenemethanol, $\gamma_{max}^{CHCl_3}$3560, 3350 cm |
| 8 | bromomethyl 4,5-dibromo-2-thienyl ketone | α-(bromomethyl)-4,5-dibromo-2-thiophenemethanol, $\gamma_{max}^{CHCl_3}$3570, 3300 cm$^{-1}$ |
| 9 | bromomethyl 3,4-dichloro-2-thienyl ketone | α-(bromomethyl)-3,4-dichloro-2-thiophenemethanol, $\gamma_{max}^{CHCl_3}$3575, 3350, 3120, 1345, 1075 cm$^{-1}$ |
| 10 | bromomethyl 4,5-dichloro-2-thienyl ketone | α-(bromomethyl)-4,5-dichloro-2-thiophenemethanol, $\gamma_{max}^{CHCl_3}$3570, 3350, 1540, 1040 cm$^{-1}$ |
| 11 | bromomethyl 3,4-dimethoxy-2-thienyl ketone | α-(bromomethyl)-3,4-dimethoxy-2-thiophenemethanol, $\gamma_{max}^{CHCl_3}$3560, 3400, .3130 cm$^{-1}$ |
| 12 | 1-bromoethyl 5-chloro-2-thienyl ketone | α-(1-bromomethyl)-5-chloro-2-thiophenemethanol |
| 13 | bromomethyl 5-methyl 2-thienyl ketone | α-(bromomethyl)-5-methyl-2-thiophenemethanol, nmr (CDCl$_3$) δ 2.47 (m, 4H), 3.6 (m, 2H), 5.0 (m, 1H), 6.8 (m, 2H) |
| 14 | bromomethyl 5-phenyl-2-thienyl ketone | α-(bromomethyl)-5-phenyl-2-thiophenemethanol, nmr (CDCl$_3$) δ 2.75 (1H), 3.65 (m, 2H), 5.1 (m, 1H), 6.9 – 7.65 (m, 7H) |

Example 15

α-{[(3,4-Dimethoxyphenethyl)amino]methyl}-2-thiophenemethanol (ArCHOR$^1$CHR$^2$NR$^3$R$^4$; Ar = 2-thienyl, R$^1$,R$^2$and R$^3$ = H and R$^4$ = 3,4-dimethoxyphenethyl)

A solution of the halohydrin, α-(bromomethyl)-2-thiophenemethanol (11.4 g, 0.055 mole), described in Example 4, and the primary amine, 3,4-dimethoxyphenethylamine (15 g, 0.083 mole), in 200 ml toluene is heated at reflux for 12 hr. The mixture is cooled to 25° C, shaken with 10% NaOH and the layers separated. The aqueous layer is extracted with chloroform and the combined organic phases washed with water and brine, dried (K$_2$CO$_3$) and concentrated. The resulting dark brown oil is purified by chromatography on silica gel to give the title compound as an oil; nmr (CDCl$_3$) 2.9 (m, 6H), 3.45 (2H), 3.85 (s, 6H), 5.05 (m, 1H), 6.7 – 7.3 (m, 6H).

The oxalic acid additional salt (oxalate) of the title compounds has mp 154° – 155° C.

EXAMPLE 16

α- [(3,4-Dimethoxyphenethyl)amino]methyl 5-methyl-2-thiophenemethanol (ArCHOR$^1$CHR$^2$NR$^3$R$^4$; Ar = 5-methyl-2-thienyl, R$^1$, R$^2$ and R$^3$ = H and R$^4$ = 3,4-dimethoxyphenethyl)

A solution of the halohydrin, α-(bromomethyl)-5-methyl-2-thienylmethanol (5.0 g, 0.0226 mole), described in Example 13, and the primary amine, 3,4-dimethoxyphenethylamine (6.2 g, 0.0339 mole), in 30 ml of dioxane is heated at reflux for 3 hr. The mixture is cooled to room temperature, diluted with 200 ml of chloroform and shaken with 10% NaOH. The organic phase is separated and washed with water and brine, dried (K$_2$CO$_3$) and concentrated to give a light brown oil. The concentrate is subjected to chromatography on silica gel using methanol-chloroform (1:9) as the eluant. Concentration of the first fractions affords β-(3,4-dimethoxyphenethylamino)-5-methyl-2-thienylethanol; nmr (CDCl$_3$) δ2.27 (s, 2H), 2.47 (s, 3H), 2.8 (m, 3H), 3.7 (m, 2H), 3.87 (s, 6H) and 6.75 (m, 5H), and isomer of the title compound; the oxalic acid addition salt of this isomer having mp 108° – 110° C. Concentration of the following second fractions affords the title compound; nmr (CDCl$_3$) δ2.45 (s, 3H), 3.0 (m, 6H), 3.85 (s, 6H), 4.45 (2H), 5.1 (t, J = 6, 2H), 6.8 (m, 5H); the oxalic acid addition salt thereof having mp 160° C.

By following the procedures of Examples 15 and 16 and using the appropriate halohydrin and the appropriate primary or secondary amine, other thiopene ethanolamines of this invention are obtained. Examples of such thiophene ethanolamines are listed in the following table together with the requisite starting materials. The halohydrin starting materials are noted by the example in which they are prepared.

| EXAMPLE | EXAMPLE IN WHICH HALOHYDRIN IS PREPARED | AMINE OF FORMULA NHR$^3$R$^4$ | THIOPHENE ETHANOLAMINE OF FORMULA ArCHOHCHR$^2$NR$^3$R$^4$ |
|---|---|---|---|
| 17 | 4 | 1-(o-tolyl)-piperazine (CDCl$_3$) δ 2.3 (s, 3H), 2.9 | α-(2-thienyl)-4-(o-tolyl)-1-piperazineethanol; mp 81 – 86° C; nmr (m, 10H), 4.0 (broad s, 1H), 5.1 (t, J = 7, 1H), 7.2 (m, 7H); the hydrochloric acid addition salt (hydrochloride) has mp 221° C |
| 18 | 13 | 3,4-(methylenedioxy)phenethylamine | 5-methyl-α- [3,4-(methylenedioxy)-phenethyl]amino methyl-2-thiophenemethanol, mp 93 – 94° C; nmr (CDCl$_3$) δ 2.42 (s, 3H), 2.8 (m, 6H), 3.1 (s, 2H), 4.9 (t, J = 6, 1H), 5.9 (s, 2H), 6.7 (m, 5H); the hydrochloric acid addition salt has mp 183 – 185° C, nmr (DMSO-d$_6$) δ 2.49 (s, 3H) |
| 19 | 14 | 3,4-dimethoxy-phenethylamine | α- [(3,4-dimethoxyphenethyl)-amino]methyl -5-phenyl-2-thiophenemethanol; nmr (CDCl$_3$) δ 2.9 (m, 6H), 3.16 (s, 2H), 3.82 (s, 6H), 5.0 (m, 1H), 6.75– |

-continued

| EXAMPLE | EXAMPLE IN WHICH HALOHYDRIN IS PREPARED | AMINE OF FORMULA NHR³R⁴ | THIOPHENE ETHANOLAMINE OF FORMULA ArCHOHCHR²NR³R⁴ |
|---|---|---|---|
| 20 | 11 | isopropylamine | 7.7 (m, 10H); corresponding hydrochloric acid addition salt has mp 185° C (dec) 3,4-dimethoxy-α-(isopropyl-aminomethyl)-2-thiophenemethanol; mp 74 – 75° C; the hydrochloric acid addition salt has mp 102–103° C; the corresponding isomer, 3,4-dimethoxy-β-(isopropylamino)-2-thiopheneethanol has bp 110° C/0.5 mm |
| 21 | 10 | 3,4-dimethoxy-phenethylamine | 4,5-dichloro-α- [(3,4-dimethoxy-phenethyl)amino]methyl -2-thio-phenemethanol; $\gamma_{max}^{CHCl_3}$ 3600, 1595 1515, 1465 cm⁻¹; the hydrochloric acid addition salt has mp 160 – 161° C |
| 22 | 10 | 2-(indol-3-yl)-ethylamine-(tryptamine) | 4,5-dichloro-α [(2-indol-3-ylethyl)amino]methyl -2-thio-phenemethanol; mp 43 – 45° C; the hydrochloric acid addition salt has mp 204 – 205° C |
| 23 | 10 | 3,4,5-trimethoxy-phenethylamine | 4,5-dichloro-α- [3,4,5-tri-methoxyphenethyl)amino]methyl -2-thiophenemethanol; nmr (CDCl₃) δ 2.75 (m, 6H), 2.90 (s, 2H), 3.80 (s, 9H), 4.75 (m, 1H), 6.33 (s, 2H), 6.66 (s, 1H); the hydrochloric acid addition salt has mp 167 – 168° C |
| 24 | 10 | α-[1-(methyl-amino)ethyl]-benzyl alcohol (d,l-ephedrine) | 4,5-dichloro-α- [N-methyl-N-(β-hydroxy-α-methylphenethyl)-amino]methyl -2-thiophene-methanol; nmr (CDCl₃) δ 1.08 (d, 3H), 6.60 (s, 1H), 7.30 (s, 5H); the hydrochloric acid addition salt has mp 63 – 65° C |
| 25 | 10 | p-hydroxy-phenethylamine (tyramine) | 4,5-dichloro- [p-hydroxyphen-ethyl)amino]methyl -2-thiophene-methanol; nmr (CDCl₃) δ 2.75 (m, 6H), 4.70 (s, 3H), 4.73 (t, 1H); the hydrochloric acid addition salt has mp 180 – 181° C |
| 26 | 10 | p-chloro-phenethylamine | 4,5-dichloro-α- [(p-chlorophen-ethyl)amino]methyl -2-thio-phenemethanol; mp 107 – 110° C; the hydrochloric acid addition salt has mp 175 – 176° C |
| 27 | 10 | p-methyl-phenethylamine | 4,5-dichloro-α- [(p-methyl-phenethyl)amino]methyl -2-thiophenemethanol; mp 92 – 94° C; the hydrochloric acid addition salt has mp 231° C (dec) |
| 28 | 10 | p-methoxy-phenethylamine | 4,5-dichloro-α-[(p-methoxy-phenethyl)amino]methyl -2-thiophenemethanol; mp 95 – 100° C; the hydrochloric acid addition salt has mp 202° C |
| 29 | 10 | 1-(p-methoxy-phenyl)piperazine | α-(4,5-dichloro-2-thienyl)-4-(p-methoxyphenyl)-1-piper-azineethanol; mp 126 – 128° C; the dihydrochloric acid addition salt has mp 213 – 215° C (dec) |
| 30 | 10 | 3,4-(methyl-enedioxy)-phenethylamine | 4,5-dichloro-α- [(3,4-methyl-enedioxy)phenethyl]amino methyl-2-thiophenemethanol; mp 99 – 103° C; the hydrochloric acid addition salt has mp 215° C (dec) |
| 31 | 12 | isopropyl-amine | 5-chloro-α-[1-(isopropylamino)-ethyl]-2-thiophenemethanol; $\gamma_{max}^{CHCl_3}$ 3300, 1460, 1145, 1130, 1060, 995 cm⁻¹; the hydrochloric acid addition salt has mp 200° C (dec); two corresponding isomers erythro- and threo-5-chloro-β-(isopropylamino)-α-methyl-2-thiopheneethanol have $\gamma_{max}^{CHCl_3}$ 1450, 1120, 1060, 990 cm⁻¹ and $\gamma_{max}^{CHCl_3}$ 3400, 1450, 1065, 990 cm⁻¹, respectively. |

EXAMPLE 32

N-(3,4-Dimethoxyphenethyl)-β-methoxy-2-thiopheneethylamine (ArCHO$^1$CHR$^2$NR$^3$R$^4$; Ar = 2-thienyl, R$^1$ = CH$_3$, R$^2$ and R$^3$ = H and R$^4$ = 3,4-dimethoxyphenethyl)

A solution of the halohydrin, α-bromomethyl-2-thiophenemethanol (10.0 g, 0.048 mole), described in Example 4, and p-toluenesulfonic acid (1.0 g) in 100 ml of the lower alkanol methanol, is heated at reflux for 5 hr. The mixture is concentrated and the concentrate extracted with ether. The ether extract is washed with water and brine, dried (MgSO$_4$) and concentrated to yield a brown liquid which is purified by chromatography on silica gel to give α-(bromomethyl)-2-thiophenemethanol methyl ether; nmr (CDCl$_3$) δ3.36 (s, 3H), 3.58 (m, 2H), 4.68 (t, J = 6.5, 1H), 7.02 (m, 1), 7.05 (m, 1H), 7.31 (m, 1H).

A solution of the latter compound (15.0 g, 0.068 mole) and the amine, 3,4-dimethoxyphenethylamine (18.5 g, 0,102 mole) in 200 ml toluene is heated at reflux for 21 hr. The mixture is cooled to room temperature, shaken with 200 ml 5% NaOH and extracted with chloroform. The combined organic extracts are washed with water and brine, dried (K$_2$CO$_3$) and concentrated to give a brown liquid. The liquid is purified by chromatography to yield the title compound; $\gamma_{max}^{CHCl_3}$ 3290, 2980, 2910, 2820, 1510, 1260 cm$^{-1}$.

The oxalic acid addition salt of the title compound has mp 210° C.

By following the procedure of Example 32 and using the halohydrins, for example, those described in Examples 4 – 14, together with the appropriate lower alkanol and amine, the corresponding lower alkyl ethers of the thiophene ethanolamine of this invention are obtained, for example, the corresponding lower alkyl ethers of the thiophene ethanolamines of Examples 15 – 31.

EXAMPLE 33

α-{[N-(3,4-dimethoxyphenethyl)-N-methylamino]}-5-methyl-2-thiophenemethanol (ArCHOR$^1$CHR$^2$NR$^3$R$^4$;Ar = 5-methyl-2-thienyl, R$^1$ and R$^2$ = H, R$^3$ = CH$_3$ and R$^4$ = 3,4-dimethoxyphenethyl)

A solution of α{(3,4-dimethoxyphenethyl)amino]-methyl}-5-methyl-2-thiophenemethanol (2.29 g, 0.007 mole), described in Example 16, and the lower alkyl halide, iodomethane (9.94 g, 0,07 mole), in 70 ml benzene is stirred at 25° C for 3 days. The mixture is concentrated under reduced pressure. The residual oil is taken up in methanol and made alkaline with 10% NaOH. The mixture is extracted with chloroform. The extract is washed with water, dried (K$_2$CO$_3$) and concentrated to give a yellow oil, which is purified by chromatography to give the title compound; nmr (CDCl$_3$) δ2.41 (s, 3H), 2.46 (s. 3H), 2.6 – 2.8 (m, 6H), 3.68 (s, 1H), 3.83 (s, 3H), 3.88 (s, 3H), 4.88 (t, 1H), 6.6 – 6.9 (m, 5H).

The oxalic acid addition salt has mp 149° C.

By following the procedure of Example 33 and using the appropriate secondary amine, namely a thiophene ethanolamine in which R$^3$ is hydrogen, for example, those described in Example 15 to 23, together with the appropriate lower alkyl halide, the corresponding thiophene ethanolamines in which R$^3$ is lower alkyl are obtained.

EXAMPLE 34

α-(Isopropylaminomethyl)-5-methoxy-2-thiophenemethanol (ArCHOR$^1$CHR$^2$NR$^3$R$^4$; Ar = 5-methoxy-2-thienyl, R$^1$, R$^2$ and R$^3$ = H and R$^4$ = isopropyl)

2-Methoxythiophene (15.4 g) is dissolved in 100 ml anhydrous THF and butyl lithium (0.135 moles) in hexane is added dropwise. The solution is stirred at room temperature 15 hr and then heated at reflux for 1 hr. After cooling, the clear solution is transferred to a dropping funnel by means of a siphon. The solution of thienyl lithium is added dropwise to a solution of diethyl oxalate (19.7 g) in 150 ml THF at −78° C. After stirring 2 hr at −78° C, the mixture is brought to −10° C and treated with saturated NH$_4$Cl solution. The aqueous fraction is separated and extracted several times with ether. The combined ether extracts are washed with water and brine, dried (MgSO$_4$) and concentrated. Chromatography on silica gel (eluant = benzene) gives 5-methoxy-2-thiopheneglyoxylic acid ethyl ester (2; X$^1$ = CH$_3$O, X$^2$ and X$^3$ = H and R$^{10}$ = C$_2$H$_5$); mp 136 –137° C after recrystallization from benzene-hexane.

The latter ester (25 g) is stirred in 500 ml of 5% aqueous KOH in methanol (250 ml H$_2$O, 250 ml CH$_3$OH, 25 g KOH) at room temperature for about 2 hr. The mixture is diluted with water and extracted several times with ether to remove all neutral material. The aqueous fraction is cooled with crushed ice, acidified with 10% HCl and extracted with ether. The ether extract is washed with water and brine, dried (MgSO$_4$) and concentrated to give 5-methoxy-2-thiopheneglyoxylic acid (3; X$^1$ = CH$_3$O, X$^2$ and X$^3$ = H and R$^{10}$ = H); $\gamma_{max}^{CHCl_3}$ 3000, 1630, 1625, 1530 cm$^{-1}$.

The latter acid (14.0 g) and triethylamine (i.1 g) are dissolved in 100 ml anhydrous THF and cooled to 0° C under a nitrogen atmosphere. Methyl chloroformate (8.5 g) in 5 ml THF is added dropwise and the solution is stirred for 2 hr at 0° C. After this time, isopropylamine (30 ml) is added dropwise and the solution is again stirred for 2 hr at 0° C. The reaction mixture is then poured onto water, separated and the aqueous fraction is extracted several times with ether. The ether fractions are washed with water and brine, dried (MgSO$_4$) and concentrated. The crude product is subjected to chromatography on silica gel (750 g, benzene:ethyl acetate, 95:5). Evaporation of the eluate and recrystallization of the residue from hexane-benzene gives N-isopropyl-5-methoxy-2-thiopheneglyoxylamide; mp 72° – 73° C.

To freshly distilled boron trifluoride etherate (61.0 mmoles) dissolved in 30 ml anhydrous ether, distilled epichlorohydrin (4.19 g, 46.0 mmoles) is added at such a rate to cause the solution to reflux. After addition, the solution is heated at reflux for 1.5 hr with vigorous stirring. The reaction mixture is cooled and most of the ether is removed with a pipette and the solid residue is dried with a stream of dry nitrogen. Anhydrous methylene chloride (50 ml) and the N-isopropyl-5-methoxy-2-thiopheneglyoxylamide (8.0 g, 39.0 mmole), described above, is added and the solution is stirred at room temperature for 56 hr. The methylene chloride is evaporated and replaced with 50 ml anhydrous methanol. The solution is cooled to 0° C. and sodium borohydride (4.0 g) is added portionwise over a period of 4 hr. The mixture is brought to room temperature, stirred for 24 hr then quenched with ice-water. The aqueous solution is extracted several times with ether. The combined ether extract are washed with water and brine, dried (MgSO₄) and concentrated. The product is purified by chromatography on silica gel (400 g, chloroformmethanol, 8:2). Evaporation of the eluate and recrystallization of the residue from hexane gives the title compound; mp 81° C, $\gamma_{max}^{CHCl_3}$ 3300, 3100, 1650, 1505, 1220 cm$^{-1}$.

The oxalic acid addition salt of the title compound has mp 100° – 101° C.

We claim:

1. A compound of the formula

ArCHOR$^1$CHR$^2$NR$^3$R$^4$ in which Ar is selected from the group consisting of 2-thienyl, 5-(lower alkyl)-2-thienyl, 5-phenyl-2-thienyl and 4,5-dichloro-2-thienyl; R$^1$ is hydrogen or lower alkyl; R$^2$ is hydrogen or lower alkyl; R$^3$ is hydrogen or lower alkyl; and R$^4$ is a substituted phenethyl of the formula

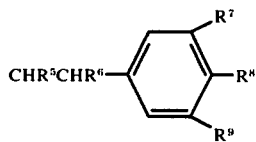

wherein R$^5$ is hydrogen or lower alkyl, R$^6$ is hydrogen or hydroxy and R$^7$, R$^8$ and R$^9$ are the same or different selected from the group consisting of hydrogen, lower alkyl, lower alkoxy, hydroxy and halo; and the acid addition salts thereof with pharmaceutically acceptable acids.

2. α{[(3,4-Dimethoxyphenethyl)amino]methyl}-2-thiophenemethanol oxalate, as claimed in claim 1.

3. α{[(3,4-Dimethoxyphenethyl)amino]methyl}-5-methyl-2-thiophenemethanol, as claimed in claim 1.

4. α-{[(3,4-Dimethoxyphenethyl)amino]methyl}-5-methyl-2-thiophenemethanol oxalate, as claimed in claim 1.

5. α-{[(3,4-dimethoxyphenethyl)amino]methyl}-5-phenyl-2-thiophenemethanol, as claimed in claim 1.

6. α-{[3,4-dimethoxyphenethyl)amino]methyl}-5-phenyl-2-thiophenemethanol hydrochloride, as claimed in claim 1.

7. 4,5-Dichloro-α-{[(3,4-dimethoxyphenethyl)amino]methyl}-2-thiophenemethanol, as claimed in claim 1.

8. 4,5-Dichloro-α-{[(3,4-dimethoxyphenethyl)amino]methyl}-2-thiophenemethanol hydrochloride, as claimed in claim 1.

9. 4,5-Dichloro-α{[(3,4,5-trimethoxyphenethyl)amino]methyl}-2-thiophenemethanol, as claimed in claim 1.

10. 4,5-Dichloro-α-{[(3,4,5-trimethoxyphenethyl)amino]methyl}-2-thiophenemethanol hydrochloride, as claimed in claim 1.

11. 4,5-Dichloro-α-{[N-methyl-N-(B-hydroxy-α-methylphenethyl)amino]methyl}-2-thiophenemethanol, as claimed in claim 1.

12. 4,5-Dichloro-α-{[N-methyl-N-(B-hydroxy-αmethylphenethyl)amino]methyl}-2-thiophenemethanol hydrochloride, as claimed in claim 1.

13. 4,5-Dichloro-{[p-hydroxyphenethyl)amino]methyl}-2-thiophenemethanol, as claimed in claim 1.

14. 4,5-Dichloro-{[p-hydroxyphenethyl)amino]methyl}-2-thiophenemethanol hydrochloride, as claimed in claim 1.

15. 4,5-Dichloro-α-{[(p-chlorophenethyl)amino]methyl}-2-thiophenemethanol, as claimed in claim 1.

16. 4,5-Dichloro-α{[-(p-chlorophenethyl)amino]-Methyl}-2-thiophenemethanol hydrochloride, as claimed in claim 1.

17. 4,5-Dichloro-α-{[(p-methylphenethyl)amino]methyl}-2-thiophenemethanol, as claimed in claim 1.

18. 4,5-Dichloro-α-{[(p-methylphenethyl)amino]methyl}-2-thiophenemethanol hydrochloride, as claimed in claim 1.

19. 4,5-Dichloro-α-{[(p-methoxyphenethyl)amino]methyl}-2-thiophenemethanol, as claimed in claim 1.

20. 4,5-Dichloro-α-{[(-methoxyphenethyl)amino]methyl}-2-thiophenemethanol hydrochloride, as claimed in claim 1.

21. N-(3,4-Dimethoxyphenethyl)-β-methoxy-2-thiopheneethylamine, as claimed in claim 1.

22. N-(3,4-Dimethoxyphenethyl)-β-methoxy-2-thiopheneethylamine oxalate, as claimed in claim 1.

23. α{[N-(3,4-Dimethoxyphenethyl)-N-methylamino]methyl}-5-methyl-2-thiopenemethanol, as claimed in claim 1.

24. α-{[N-(3,4-Dimethoxyphenethyl)-N-methylamino]methyl}-5-methyl-2-thiophenemethanol oxalate, as claimed in claim 1.

25. A compound of the formula

ArCHOR$^1$CHR$^2$NR$^3$R$^4$ in which Ar is selected from the group consisting of 2-thienyl, 5-methyl-2-thienyl, 5-phenyl-2-thienyl and 4,5-dichloro-2-thienyl; R$^1$ is hydrogen or methyl; R$^2$ is hydrogen; R$^3$ is hydrogen or methyl; R$^4$ is 3,4-dimethoxyphenethyl, 3,4,5-trimethoxyphenethyl, β-hydroxy-α-methyl-phenethyl, p-hydroxyphenethyl, p-chlorophenethyl, p-methylphenethyl or p-methoxyphenethyl; and the acid addition salts thereof with pharmaceutically acceptable acids, as claimed in claim 1.

26. α-{(3,4-Dimethoxyphenethyl)amino]methyl}--2-thiophenemathanol, as claimed in claim 1.

* * * * *